United States Patent
Li et al.

(10) Patent No.: US 8,981,133 B2
(45) Date of Patent: Mar. 17, 2015

(54) ALKYLENE OXIDE SEPARATION SYSTEMS, METHODS, AND APPARATUSES

(75) Inventors: Xiangmin Li, Glen Mills, PA (US); David W. Leyshon, West Chester, PA (US); Te Chang, West Chester, PA (US)

(73) Assignees: Lyondell Chemical Technology, L.P., Houston, TX (US); Equistar Chemicals, LP, Houston, TX (US)

( * ) Notice: Subject to any disclaimer, the term of this patent is extended or adjusted under 35 U.S.C. 154(b) by 687 days.

(21) Appl. No.: 13/155,136

(22) Filed: Jun. 7, 2011

(65) Prior Publication Data

US 2012/0312680 A1    Dec. 13, 2012

(51) Int. Cl.
*B01D 3/40* (2006.01)
*C07D 301/32* (2006.01)
*C07D 303/04* (2006.01)
*C07D 301/19* (2006.01)

(52) U.S. Cl.
CPC ............... *C07D 303/04* (2013.01); *B01D 3/40* (2013.01); *C07D 301/19* (2013.01); *C07D 301/32* (2013.01)
USPC ............... 549/541; 203/2; 203/39; 203/53; 203/68; 203/70; 549/529

(58) Field of Classification Search
CPC .......... B01D 3/40; B01D 3/42; B01D 5/0063; C07D 301/19; C07D 301/32; C07D 303/04
USPC .................. 203/2, 39, 53, 57, 68, 70, 94, 98; 549/529, 541
See application file for complete search history.

(56) References Cited

U.S. PATENT DOCUMENTS

| | | | |
|---|---|---|---|
| 2,550,847 A | 5/1951 | Mitchell et al. | |
| 2,622,060 A | 12/1952 | Robeson et al. | |
| 3,287,234 A * | 11/1966 | Steel et al. | 203/49 |
| 3,338,800 A | 8/1967 | Binning et al. | |
| 3,350,417 A | 10/1967 | Binning et al. | |
| 3,464,897 A | 9/1969 | Jubin, Jr. | |
| 3,477,919 A | 11/1969 | Lichtenwalter et al. | |
| 3,607,669 A | 9/1971 | Jubin, Jr. | |
| 3,632,482 A * | 1/1972 | Hoory et al. | 203/56 |
| 3,843,488 A | 10/1974 | Schmidt | |
| 3,881,996 A | 5/1975 | Schmidt | |
| 3,947,476 A | 3/1976 | Biola et al. | |
| 4,140,588 A | 2/1979 | Schmidt | |
| 4,379,025 A * | 4/1983 | Yudovich et al. | 203/14 |
| 4,402,794 A * | 9/1983 | Nemet-Mavrodin et al. | 203/14 |
| 4,691,034 A | 9/1987 | Sanderson et al. | |
| 4,691,035 A | 9/1987 | Sanderson et al. | |

(Continued)

FOREIGN PATENT DOCUMENTS

WO    2010014187    *  2/2010

Primary Examiner — Virginia Manoharan

(57) ABSTRACT

The disclosure relates to a process for separating propylene oxide for a crude propylene oxide stream, for example an intermediate stream from a PO/TBA process. The crude propylene oxide stream can be passed through an extractive distillation column. The distillation column is operated at a pressure in a range of greater than 25 up to 50 psig, and/or at a temperature in a range of from 70 to 150 degrees Celsius using $C_8$-$C_{20}$ paraffin as extractive solvent with an overhead distillate water wash drum. The crude propylene oxide stream include from 0.001 to 0.1 wt % methanol, based on the total composition of the crude propylene oxide stream. The systems, methods, and apparatuses can produce a propylene oxide stream having less formaldehyde and acetaldehyde than the prior art.

21 Claims, 3 Drawing Sheets

(56) References Cited

U.S. PATENT DOCUMENTS

| | | |
|---|---|---|
| 5,000,825 A | 3/1991 | Shih et al. |
| 5,006,206 A | 4/1991 | Shih et al. |
| 5,106,458 A | 4/1992 | Meyer et al. |
| 5,107,002 A | 4/1992 | Shih |
| 5,116,466 A | 5/1992 | Marquis et al. |
| 5,116,467 A | 5/1992 | Marquis et al. |
| 5,139,622 A | 8/1992 | Marquis et al. |
| 5,145,561 A | 9/1992 | Marquis et al. |
| 5,145,563 A | 9/1992 | Culbreth, III et al. |
| 5,154,803 A | 10/1992 | Marquis et al. |
| 5,154,804 A | 10/1992 | Marquis et al. |
| 5,160,587 A | 11/1992 | Marquis et al. |
| 5,340,446 A | 8/1994 | Nelson et al. |
| 5,620,568 A | 4/1997 | Smith et al. |
| 5,849,938 A | 12/1998 | Rueter et al. |
| 5,958,192 A | 9/1999 | Morford |
| 5,973,171 A | 10/1999 | Cochran et al. |
| 6,024,840 A * | 2/2000 | Rueter ............... 203/50 |
| 6,500,311 B1 * | 12/2002 | Sawyer ............... 203/44 |
| 6,559,248 B2 | 5/2003 | Hendriksen et al. |
| 7,105,687 B1 | 9/2006 | Chang |
| 7,138,535 B1 | 11/2006 | Whitman et al. |
| 7,285,187 B2 * | 10/2007 | Oku et al. ............ 203/3 |
| 7,323,579 B2 * | 1/2008 | Gobbel et al. ......... 549/541 |
| 7,550,610 B1 | 6/2009 | Chang et al. |
| 7,615,654 B2 | 11/2009 | Le-Khac et al. |
| 7,649,102 B2 | 1/2010 | Chang et al. |
| 7,687,647 B2 | 3/2010 | Chang |
| 7,692,031 B2 | 4/2010 | Goebbel et al. |
| 7,705,167 B2 | 4/2010 | Shinohara et al. |
| 7,741,498 B2 | 6/2010 | Chang et al. |
| 7,863,468 B2 | 1/2011 | Schindler et al. |
| 2007/0238888 A1 * | 10/2007 | Goebbel et al. ....... 549/541 |
| 2012/0077996 A1 * | 3/2012 | Sawyer ............... 549/529 |

* cited by examiner

ALKYLENE OXIDE SEPARATION SYSTEMS, METHODS, AND APPARATUSES

FIELD OF THE INVENTION

The present invention relates to a process for the purification and recovery of propylene oxide which is formed from epoxidation of propylene with hydroperoxides derived from oxidation of isobutane, ethyl benzene or cumene. In particular, the process improves the separation of light aldehydes, such as formaldehyde and acetaldehyde, from propylene oxide.

BACKGROUND OF THE INVENTION

Approximately 14.5 billion pounds of propylene oxide are produced every year. Propylene oxide has many uses. Between 60 and 70% of all propylene oxide is converted to polyether polyols for the production of polyurethane plastics. About 20% of propylene oxide is hydrolyzed into propylene glycol, via a process which is accelerated either by thermal reaction or by acid or base catalysis. Other major products are polypropylene glycol, propylene glycols ethers, and propylene carbonate. To produce these end products, propylene oxide free of impurities is needed.

Methods of producing alkylene oxides including propylene oxide involve hydrochlorination and epoxidation of its corresponding olefins. The oxidates used in the epoxidation processes are derived from tertiary or secondary hydrocarbons by direct oxidation with molecular oxygen; hence, they contain oxygenate impurites and precursors. Additional oxygenate impurites are also generated in the step of epoxidation of olefins. Crude alkylene oxides, such as propylene oxide, particularly those produced from epoxidation with hydrocarbon oxidates contain a significant amount of oxygenated impurities difficult to separate from alkylene oxides. The impurities generally include water, acids, alcohols, aldehydes, ketones and esters. A need exists for continued improvement of systems and methods for separating propylene oxide from these impurity constituents of effluent streams of various methods of producing propylene oxide.

U.S. Pat. No. 3,338,800 teaches extractive distillation of alkylene oxides having from 3 to 18 carbon atoms with a paraffin or paraffin naphtha solvent. More particularly, this patent suggests that oxygenated impurities boiling within 5° C. of the alkylene oxide may be separated by extractive distillation using acyclic paraffinic hydrocarbons as solvents having boiling points at least 35° C. above the boiling points of the said impurities. The problem addressed by this patent is that epoxide fractions produced by the direct oxidation of ethylenically unsaturated compounds with molecular oxygen in the liquid phase contain oxygenated impurities which, because their boiling points are similar to the desired epoxide product, cannot be separated by conventional distillation techniques.

U.S. Pat. No. 3,881,996 teaches that the sequence of the fractionation steps has a major effect on the final purity of the propylene oxide obtained, particularly with regard to aldehyde content. Substantially improved results are obtained when the removal of acetaldehyde and lower boiling materials precedes the step in which propylene oxide is separated from propionaldehyde and higher boiling material. This result is highly unusual and is not in accord with customary calculable performance of fractional distillation equipment. The inventor believes that chemical reactions may be occurring during distillation which interfere with the normal mass transfer steps and thereby produce anomalous results. However, the scientific reasoning is not offered.

U.S. Pat. Nos. 3,464,897 and 3,843,488 teach using hydrocarbon solvents of 8-20 carbon atoms can effective remove C5-C7 impurities from propylene oxide in extractive distillation. U.S. Pat. No. 3,607,669 teaches a method for separating propylene oxide from water by distilling the mixture in the presence of acyclic or cyclic paraffin containing 8 to 12 carbon atoms by breaking water-propylene oxide azeotrope at elevated pressure. There are many other U.S. Patents, such as U.S. Pat. Nos. 4,140,588, 5,000,825, 5,006,206, 5,116,466, 5,116,467, 5,139,622, 5,145,561, 5,145,563, 5,154,803, 5,154,804, 5,160,587, 5,340,446, 5,620,568, 5,958,192 and 6,559,248 introduce various solvents in extractive distillation operations for propylene oxide purification. U.S. Pat. Nos. 2,550,847, 2,622,060, 3,350,417, 3,477,919, 4,691,034, 4,691,035, 5,106,458 and 5,107,002 teach how to separate methyl formate from propylene oxide. Although these patents teach the removal of selected propylene oxide impurities, none address removal of aldehydes, particularly formaldehyde and acetaldehyde.

U.S. Pat. No. 6,024,840 uses methanol as extractive solvent to remove acetaldehyde from propylene. However, solvent methanol itself becomes close-boiling propylene oxide contaminant. U.S. Pat. No. 7,705,167 teaches using water wash propylene oxide followed by contacting aqueous phase with hydrocarbon extractive solvent and subsequent distillation. These teachings are impractical for the existing plant improvement. Because it is difficult to recover a propylene oxide containing total aldehydes below 50 ppm and free of formaldehyde, particularly for propylene oxide produced from tert-butyl hydroperoxide process, it is the objective of the present invention to provide a method applicable to the existing plants for recovering propylene oxide in a high state of purity low in aldehydes without substantial loss of propylene oxide product.

SUMMARY OF THE INVENTION

One embodiment relates to a systems, methods, and apparatuses for separating propylene oxide from a crude propylene oxide stream.

A crude propylene oxide stream, for example an intermediate stream from a PO/TBA process, can be passed through an extractive solvent lights distillation column. The crude propylene oxide stream comprises various impurities like formaldehyde, acetaldehyde, methyl formate, methanol, and water. By operating the Solvent Lights Column at a higher temperature and pressure, better rejection of aldehyde impurities to the Solvent Lights Column overhead is achieved. By reducing the methanol concentration in crude PO feed, better rejection of the aldehyde impurities to the Solvent Lights Column is also achieved. Subsequent Water Wash removes the oxygenate impurities, particularly methanol, from the overhead of Solvent Lights Column.

BRIEF DESCRIPTION OF THE DRAWINGS

These and other features, aspects, and advantages of the present invention will become better understood with reference to the following description and appended claims, and accompanying drawings where:

Figure 1:
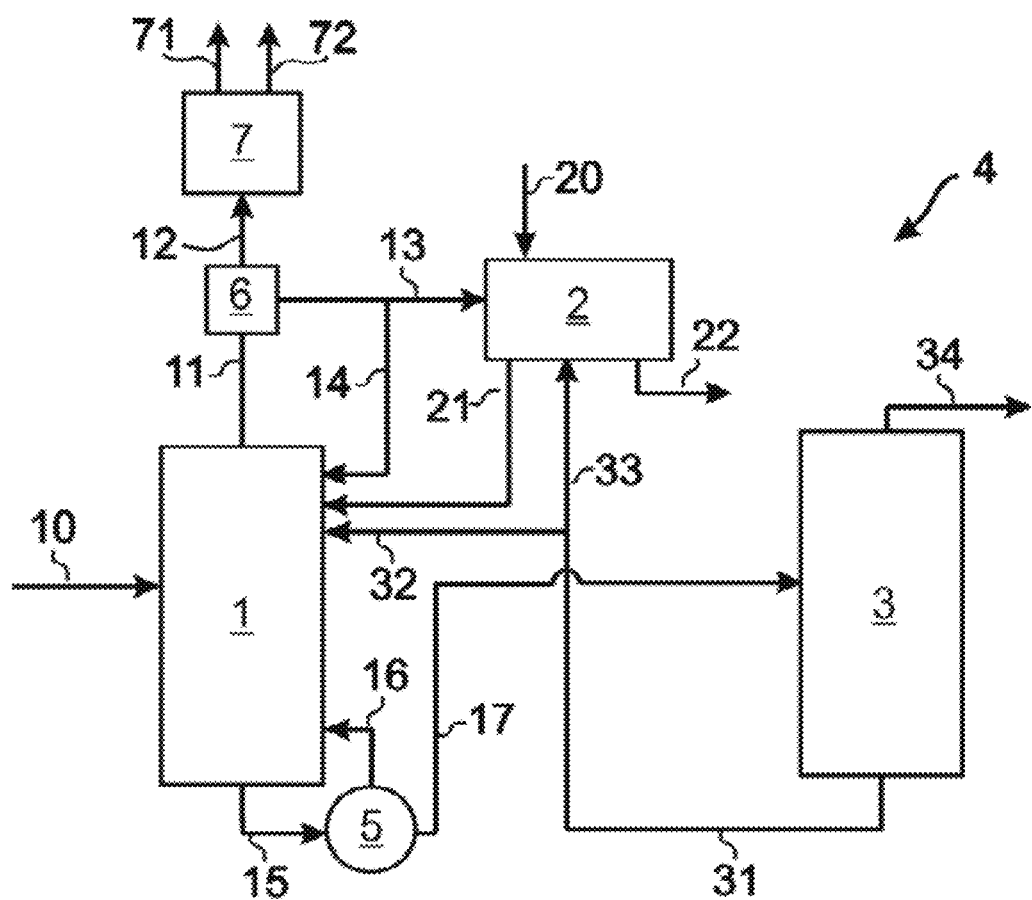
FIG. 1 is a schematic block diagram of a propylene oxide separation system according to one embodiment.

It should be understood that the various embodiments are not limited to the arrangements and instrumentality shown in the drawings.

DETAILED DESCRIPTION OF EMBODIMENTS OF THE INVENTION

The present disclosure may be understood more readily by reference to the following detailed description of preferred embodiments of the invention as well as to the examples included therein One method for producing propylene oxide (PO), also known as epoxypropane, propylene epoxide, 1,2-propylene oxide, methyl oxirane, 1,2-epoxypropane, propene oxide, methyl ethylene oxide, methylethylene oxide, will now be described. First, as shown in Formula 1, isobutane (IB), also known as 2-methylpropane, can be reacted with oxygen to form tert-butyl hydroperoxide (TBHP), also known as 2-Methylpropane-2-peroxol.

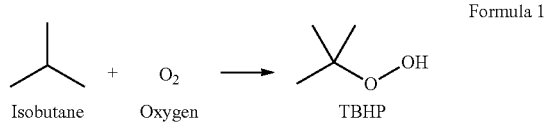

Formula 1

Isobutane    Oxygen    TBHP

Subsequently, as shown in Formula 2, propylene, also known as propene, can be reacted with TBHP in the presence of a catalyst to form PO and tert-Butanol (TBA), also known as 2-methyl-2-propanol.

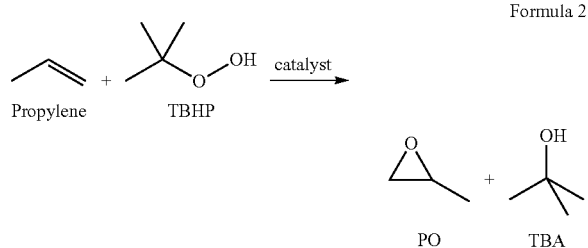

Formula 2

Propylene    TBHP

PO    TBA

Since this method produces both PO and TBA it shall be referred to as the PO/TBA process.

The PO/TBA process can also yield a variety of unwanted side products. Without wishing to be bound by theory, non-selective reactions can take place to produce the impurities. Such non-selective reactions can include, but are not limited to the reactions depicted in Formulas 3-6.

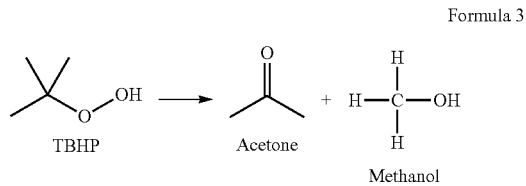

Formula 3

TBHP    Acetone    Methanol

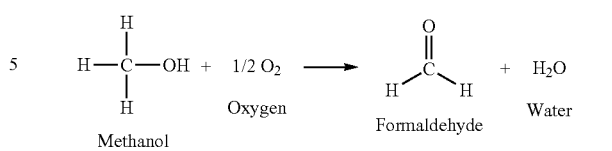

Formula 4

Methanol    Oxygen    Formaldehyde    Water

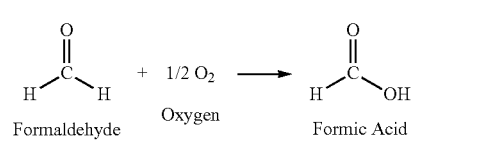

Formula 5

Formaldehyde    Oxygen    Formic Acid

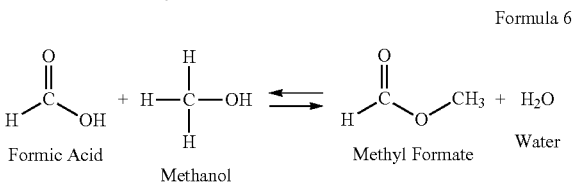

Formula 6

Formic Acid    Methanol    Methyl Formate    Water

Acetaldehyde can also be formed in the PO/TBA process. A possible mechanism for the formation of acetaldehyde is shown in Formula 7.

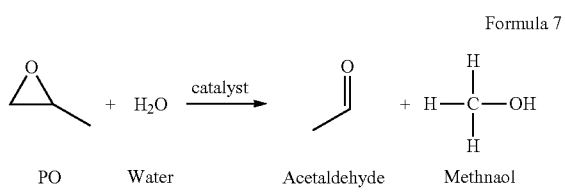

Formula 7

PO    Water    Acetaldehyde    Methnaol

The concentrations of these impurities that end up in a crude PO stream from a PO/TBA process can vary.

Methyl formate can be present in an amount within a range having a lower limit and/or an upper limit, each expressed as a weight percentage of the total composition of a crude PO stream from a PO/TBA process. The range can include or exclude the lower limit and/or the upper limit. The methyl formate lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example methyl formate can be present in an amount of greater than 0.06 weight percent of the total composition of a crude PO stream from a PO/TBA process.

Methanol can be present in an amount within a range having a lower limit and/or an upper limit, each expressed as a weight percentage of the total composition of a crude PO stream from a PO/TBA process. The range can include or exclude the lower limit and/or the upper limit. The methanol lower limit and/or upper limit can be selected from 0, 0.001, 0.002, 0.003, 0.0031, 0.0032, 0.0033, 0.0034, 0.0035, 0.0036, 0.0037, 0.0038, 0.0039, 0.0139, 0.0239, 0.0339, 0.0439, 0.0539, 0.0639, 0.0739, 0.0839, 0.0939, 0.1039, 0.1049, 0.1059, 0.1069, 0.1079, 0.1089, 0.1099, 0.1109, 0.1119, 0.1129, 0.1139, 0.1149, 0.1159, 0.116, 0.1161, 0.1162, 0.1163, 0.1164, 0.1165, 0.1166, 0.1167, 0.1168, 0.1169, 0.117, 0.1171, 0.1172, 0.1173, 0.1174, 0.1175, 0.1176, 0.1177, 0.2177, 0.3177, 0.4177, 0.5177, 0.6177, 0.7177, 0.8177, 0.9177, 1, 2, 3, 4, 5, and 10 weight percent. For example, methanol can be present in an amount greater than 0.0032 weight percent or in an amount greater than 0.1172 weight percent of the total composition of a crude PO stream from a PO/TBA process.

Acetaldehyde can be present in an amount within a range having a lower limit and/or an upper limit, each expressed as a weight percentage of the total composition of a crude PO stream from a PO/TBA process. The range can include or exclude the lower limit and/or the upper limit. The acetaldehyde lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, acetaldehyde can be present in an amount of greater than 0.03 weight percent of the total composition of a crude PO stream from a PO/TBA process.

Water can be present in an amount within a range having a lower limit and/or an upper limit, each expressed as a weight percentage of the total composition of a crude PO stream from a PO/TBA process. The range can include or exclude the lower limit and/or the upper limit. The water lower limit and/or upper limit can be selected from 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, water can be present in an amount of greater than 0.16 weight percent of the total composition of a crude PO stream from a PO/TBA process.

Formaldehyde can be present in an amount within a range having a lower limit and/or an upper limit, each expressed as a weight percentage of the total composition of a crude PO stream from a PO/TBA process. The range can include or exclude the lower limit and/or the upper limit. The formaldehyde lower limit and/or upper limit can be selected from 0, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, and 10 weight percent. For example, formaldehyde can be present in an amount of greater than 0.005 weight percent of the total composition of a crude PO stream from a PO/TBA process.

Tables 1 and 2 show exemplary concentrations of key impurities in a crude PO stream from a PO/TBA process, each expressed as a weight percentage of the total composition of a crude PO stream from a PO/TBA process.

TABLE 1

| Component | Average weight percent |
|---|---|
| MeF | 0.06 |
| Methanol | 0.1172 |
| Acetaldehyde | 0.03 |
| Water | 0.16 |
| Formaldehyde | 0.005 |

TABLE 2

| Component | Average weight percent |
|---|---|
| MeF | 0.06 |
| Methanol | 0.0032 |
| Acetaldehyde | 0.03 |
| Water | 0.16 |
| Formaldehyde | 0.005 |

Without wishing to be bound by theory, a major problem is caused by the reaction of methanol with formaldehyde. As shown in Formula 8, an aldehyde, like formaldehyde, can react with an alcohol, like methanol to form a hemiacetal. According to Formula 8, R1 and R2 can be hydrogen, or a $C_{1-10}$ alkyl.

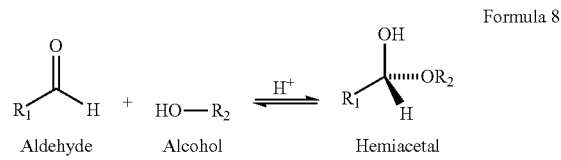

Formula 8

Formation of an acetal can occur when the hydroxyl group of a hemiacetal becomes protonated and is lost as water, as illustrated in Formula 9, wherein R1, R2, and R3 can be hydrogen, or a $C_{1-10}$ alkyl.

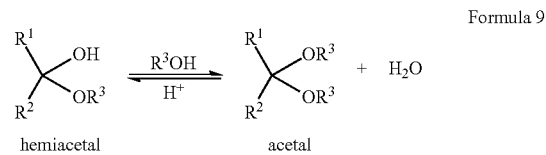

Formula 9

Both formaldehyde and methanol would be lights by themselves, but the formation of hemiacetals and acetals can make them heavy. Subsequently, these addition products can travel downstream where temperatures increase and the reaction reverses. When the reaction reverses, aldehydes can become trapped with the desired propylene oxide product.

Referring to FIG. 1, a first embodiment of the present disclosure relates to a separation system 4 for removing impurities from a crude PO stream 10 from a PO/TBA process. The crude PO stream 10 can include, but is not limited to, all of the impurities described above along with the desired product, propylene oxide. The effluent stream 10 can be fed into a solvent-lights column 1. Most of the impurities in crude PO stream 10 can be removed in an overhead stream 11.

Figure 2:
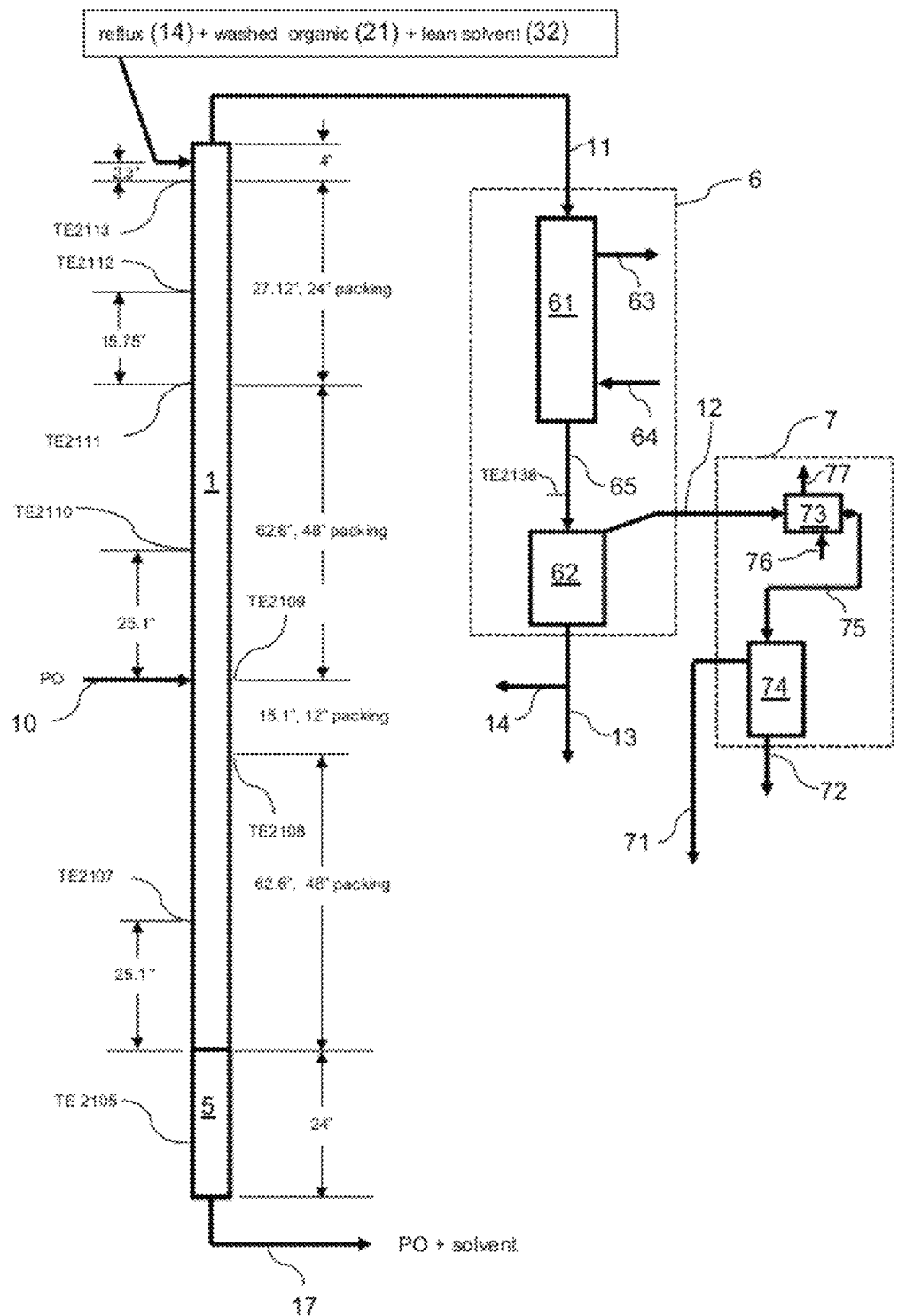
FIG. 2 is a schematic, including a solvent lights tower, according to one embodiment, as used in a pilot plant.

Referring to FIG. 2, overhead stream 11 can be passed into a cooler 61, supplied with cooling fluid via cooling inlet line 64 and cooling outlet line 63. The partially condensed outlet stream 65 from the cooler 61 flow into a reflux drum 62. Vapor stream 12 from the reflux drum 62 can be fed to a vapor condenser 73, supplied with cooling glycol via inlet 76 and outlet 77. The outlet 75 from condenser 73 can be fed into a separator 74 to produce a vapor purge stream 71 and a liquid purge stream 72.

Referring again to FIG. 1, a reflux stream 14 can be taken from wash inlet stream 13 and recycled to the solvent-lights column 1. Wash inlet stream 13 can be fed into a water wash apparatus 2. A water inlet stream 20 can also be fed into the water wash apparatus 2. Solvents recovered from the water wash apparatus 2 can be recycled via recycle line 21 to the solvent-light column 1. An aqueous purge stream 22 can also be removed from the water wash apparatus 2.

The bottom product 15 of solvent-lights column 1 can be passed through a reboiler 5. A reboiler vapor stream 16 can be fed back to the solvent-lights column 1. A reboiler bottoms product stream 17 can be added to solvent stripper column 3. An overhead product stream 34 of the solvent stripper column 3 can include the desired propylene oxide product. Overhead product stream 34 can be processed to achieve further separation of propylene oxide. A bottoms product stream 31 of the solvent stripper column 3 can be recycled to the water wash apparatus 2 via line 33 and/or to the solvent-light column 1 via line 32.

The solvent-lights column 1 will now be described in greater detail. The solvent-lights column 1 can be made of any suitable material, including but not limited to carbon steel or stainless steel. The solvent-light column 1 can include any suitable number of trays or theoretical trays, for example, about 25 theoretical stages. Feed stream 10 can be added at tray 11 to 15, counting from the bottom. A suitable packing material can be employed in the solvent-lights column to enhance vapor-liquid contact. Suitable packing materials can be made from any material including glass, metal, plastic, and ceramic. The packing can be structured or dumped. Trays such as sieve trays, bubble cap trays or valve trays can also be used.

As described below, water wash apparatus 2 is very effective in removing key light impurities such as methyl formate, formaldehyde, acetaldehyde, and methanol. This helps keep hemiacetal or acetal formation as low as possible in the solvent-lights column 1. As already discussed, hemiacetal and acetal could enter into the solvent-light bottom product stream 15 and later breakdown in downstream columns as aldehydes to contaminate the propylene oxide product.

Unexpected and beneficial results can be obtained by operating solvent-lights column 1 and/or reboiler 5 at a temperature within a range having a lower limit and/or an upper limit, each expressed in degrees Celsius. The range can include or exclude the lower limit and/or the upper limit. The reboiler temperature lower limit and/or upper limit can be selected from 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160 degrees Celsius. For example, the reboiler 5 can be operated at a temperature of 114 degrees Celsius or in a range of from 80 to 120 degrees Celsius.

Additionally or alternatively, unexpectedly beneficial results can be obtained by operating solvent-lights column 1 at a pressure within a range having a lower limit and/or an upper limit, each expressed in psig. The range can include or exclude the lower limit and/or the upper limit. The pressure lower limit and/or upper limit can be selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 psig. For example, the solvent-lights column 1 can be operated at a pressure of 30 psig or in a range of from 20 to 50 psig.

Without wishing to be bound by theory, it is believed that by operating reboiler 5 at temperatures and/or pressures in the above-recited ranges, heavies such as hemiacetal or acetal formed in solvent-lights column 1, can break down into aldehydes. These aldehydes can then be removed to the overhead of the solvent-lights column 1 and eventually be purged out via water wash apparatus 2 or via the vent purge 12 instead of staying in the column bottom and contaminating the PO product.

One embodiment of the present disclosure relates to a method for removing impurities from a crude PO stream from a PO/TBA process. The crude PO stream can have a composition as previously defined. The method can include passing the crude PO stream through a distillation column, such as solvent-lights column 1. The distillation column can be operated at the temperatures and pressures as previously defined.

Vapor Liquid Equilibrium (VLE) studies confirm that at increased pressure or temperature, acetaldehyde relative volatility to PO decreases, which indicates a more difficult aldehyde separation in the solvent-light column 1 at a higer pressure when alcohols are not present. Unexpectedly, with alcohols present, higher temperature and pressure result in a greater relative volatility of acetaldehyde relative to PO than at a lower pressure. Results of the experimental VLE studies are given in Tables 3 and 4.

Table 3 presents the results of an experiment of binary acetaldehyde-propylene oxide VLE. Data was obtained for three pressures, 14.7 psia, 29.2 psia, and 60 psia. This binary VLE data set shows a declining acetaldehyde to PO volatility at increasing pressure or temperature. Since the mixtures do not contain methanol, the effect on volatility could be only pressure or temperature although there is a possibility of acetaldehyde dimer or trimer formation. However, the acetaldehyde dimer or trimer formation equilibrium would be similar to hemiacetal/acetal equilibriums; they would be favored at low pressure/temperature. Therefore, the effect of pressure/temperature observed here could be slightly reduced. This set of data was obtained at starting acetaldehyde concentration of 5300 ppm.

TABLE 3

Relative Volatility of Acetaldehyde in Crude Propylene Oxide without methanol[1]

| Pressure (psia) | Temperature (° C.) | Component | Composition (weight percent) Vapor[2] | Composition (weight percent) Liquid[2] | K values | α (AA/PO) |
|---|---|---|---|---|---|---|
| 14.7 | 32 | AA | 0.752 | 0.421 | 1.786 | 1.791 |
|  |  | PO | 99.248 | 99.579 | 0.997 |  |
| 29.2 | 55.7 | AA | 0.717 | 0.461 | 1.556 | 1.560 |
|  |  | PO | 99.283 | 99.529 | 0.994 |  |
| 60.0 | 79.8 | AA | 0.649 | 0.418 | 1.554 | 1.557 |
|  |  | PO | 99.351 | 99.582 | 0.998 |  |

Note:
[1]Contains 0.53% Acetaldehyde
[2]Normalized

Unexpected and beneficial results can also be obtained by reducing the amount of water, methanol, and/or glycol concentration in the solvent-light column 1. With reduced methanol (MeOH) in the propylene oxide feed 10, both formaldehyde and acetaldehyde removal can be improved, as indicated by the reduced aldehyde level in solvent stripper overhead 34.

VLE (Table 4) showed that acetaldehyde relative volatility to PO declines with increased methanol concentration.

Table 4 presents VLE data for PO-acetaldehyde-methanol system, for the effect of methanol on acetaldehyde volatility in propylene oxide. The results demonstrate that at atmospheric pressure or low temperature, acetaldehyde volatility to PO declines with increasing methanol concentration in PO. As methanol concentration reaches about 2.5-3 wt %, acetaldehyde volatility to PO is approaching 1 which makes acetaldehyde inseparable from PO. When methanol concentration increases to about 4 wt %, acetaldehyde become heavier than PO with a relative volatility to PO near 0.82. This phenomenon is believed to be caused by the formation of hemiacetal and acetal at increased methanol concentration even though acetaldehyde concentration was low at only around 50 ppm. Additional VLE data were obtained at about 3 wt % methanol and elevated pressure or increased temperature. By comparing data obtained at atmospheric pressure, 16 psig and 28.7 psig, the results show that acetaldehyde volatility to PO increases with increasing pressure or temperature when methanol is present at a same methanol concentration. The equilibrium formation of hemiacetal/acetal becomes less favored at elevated temperatures. Thus, it is desirable to remove methanol first so that aldehydes will distill overhead in the solvent lights tower. If aldehydes are not completely removed, it is desirable to increase the pressure of the solvent lights tower to break the hemi-acetals, so that the aldehydes can be taken overhead.

The water wash apparatus 2 will now be described in greater detail. The overhead of Solvent Lights Column 1 (Stream 13) can be sent to water wash apparatus 2. Water wash 2 can be carried out by mixing the solvent lights column 1 overhead with water and solvent. Water supplied via wash inlet stream 20 can be used to remove the impurities from propylene oxide. A solvent (Stream 33) can be used to minimize propylene oxide loss into the water phase. Adequate mixing is required to accomplish the best impurity removal. Adequate coalescing, and enough residence time in the decanter is also necessary to minimize entrainment of the aqueous phase in the organic effluent. The organic effluent can be recycled back to the solvent lights column 1 via recycle line 21. An aqueous purge stream 22 with a high concentration of impurities can be purged from the water wash apparatus 2.

The organic effluent, stream 21, can include an amount of the aqueous phase within a range having a lower limit and/or an upper limit, each expressed as weight percentages. The range can include or exclude the lower limit and/or the upper limit. The lower limit and/or upper limit for the amount of the aqueous phase in the organic effluent of the wash can be selected from 0, 0.01, 0.02, 0.03, 0.04, 0.05, 0.1, 0.2, 0.3, 0.4, 0.5, 0.7, 1, 2, 3, 4, 5, 6, 7, 8, 9, and 10, weight percent. For example, less than 0.1% of the aqueous phase can be present in the organic effluent of the wash or 10% of the aqueous phase can be present in the organic effluent of the wash.

TABLE 4

VLE of Synthetic PO-AA-MeOH Mixtures at Atmospheric Pressure

| Run # | T (° C.) | P (mmHg) | Component | Composiiton (by weight) Vapor | Liquid | K values | α (AA/PO) |
|---|---|---|---|---|---|---|---|
| 1 | 33.3 | 755.8 | AA | 96 ppm | 56 ppm | 1.74 | 1.74 |
| | | | MeOH | — | 5 ppm | — | |
| | | | PO | 99.9904% | 99.9939% | 1.00 | |
| 2 | 33.0 | 754.3 | AA | 99 ppm | 57 ppm | 1.79 | 1.76 |
| | | | MeOH | 582 ppm | 666 ppm | 0.87 | |
| | | | PO | 99.93199% | 99.9278% | 1.00 | |
| 3 | 33.4 | 748.4 | AA | 85 ppm | 53 ppm | 1.61 | 1.61 |
| | | | MeOH | 0.3772% | 0.4984% | 0.76 | |
| | | | PO | 99.6143% | 99.4963% | 1.00 | |
| 4 | 32.8 | 747.5 | AA | 83 ppm | 51 ppm | 1.62 | 1.62 |
| | | | MeOH | 0.8165% | 1.0476% | 0.78 | |
| | | | PO | 99.1752% | 98.9493% | 1.00 | |
| 5 | 32.4 | 754.3 | AA | 68 ppm | 51 ppm | 1.35 | 1.33 |
| | | | MeOH | 2.3812% | 3.4437% | 0.69 | |
| | | | PO | 97.612% | 96.5512% | 1.01 | |
| 6* | 34.7 | 750.9 | AA | 56 ppm | 52 ppm | 1.09 | 1.08 |
| | | | MeOH | 2.6061% | 3.50% | 0.74 | |
| | | | PO | 97.3883% | 96.4856% | 1.01 | |
| 7 | 32.7 | 755.1 | AA | 44 ppm | 52 ppm | 0.86 | 0.84 |
| | | | MeOH | 3.7000% | 5.8658% | 0.63 | |
| | | | PO | 96.2956% | 94.1290% | 1.02 | |
| 8 | 33.5 | 746.9 | AA | 44 ppm | 52 ppm | 0.85 | 0.82 |
| | | | MeOH | 4.2013% | 7.1129% | 0.59 | |
| | | | PO | 95.7943% | 92.8819% | 1.03 | |
| 9* | 34.7 | 750.9 | AA | 56 ppm | 52 ppm | 1.09 | 1.08 |
| | | | MeOH | 2.6061% | 3.5092% | 0.74 | |
| | | | PO | 97.3883% | 96.4856% | 1.01 | |
| 10* | 56.4 | 16 psig | AA | 63 ppm | 48 ppm | 1.33 | 1.32 |
| | | | MeOH | 2.9799% | 3.3628% | 0.89 | |
| | | | PO | 97.0138% | 96.6325% | 1.00 | |
| 11* | 68.1 | 28.7 psig | AA | 67 ppm | 47 ppm | 1.42 | 1.42 |
| | | | MeOH | 3.2594% | 3.3560% | 0.97 | |
| | | | PO | 96.7339% | 96.6393% | 1.00 | |

*Run # 6 was conducted in a steel recirculation still.
*Runs # 9-11 were conducted in a stainless-steel still.

Key light impurities to remove are methyl formate, formaldehyde, acetaldehyde, and methanol. Most of these impurities can be removed by a combination of vapor purge 12 and an aqueous purge 22 from water wash apparatus 2 of the solvent-lights column overhead stream 11. Lab water wash tests have demonstrated the effective removal of these key light impurities.

The solvent stripper 3 will now be described in greater detail. The solvent stripper 3 can be made of any suitable material, including but not limited to stainless steel or carbon steel. The solvent stripper 3 can include any suitable number of trays or theoretical trays, for example, about 10 trays. Reboiler bottoms product stream 17 can be added at tray 1-10, preferably at tray 5. A suitable packing material can be employed in the solvent-light column to enhance vapor-liquid contact. Suitable packing materials can be made from any material including glass, metal, plastic, and ceramic. If packing is used, it can be structured or dumped. If trays are used, then can be sieve trays, bubble cap trays or valve trays.

Figure 3:
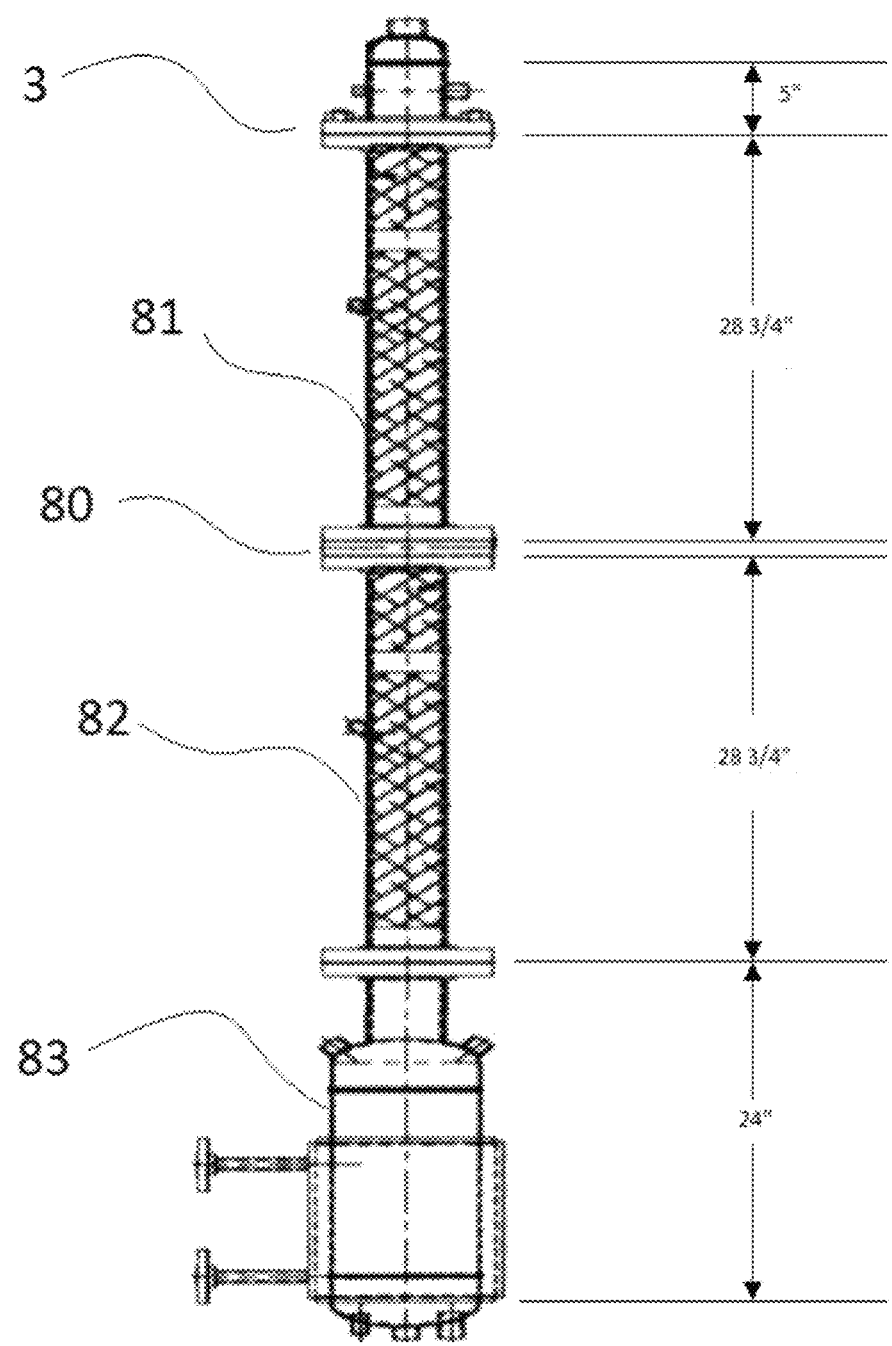
FIG. 3 is a schematic of a solvent stripper column, according to one embodiment, as used in a pilot plant.

Referring to FIG. 3, the solvent stripper column 3, according to one embodiment as used in a pilot plant, is depicted in greater detail. The solvent stripper column 3 was made from 3" Schedule 40 pipe. The entire height including the reboiler 83 was 88 inches tall. The solvent stripper column 3 included a first packed section 81 and a section packed section 82, each packed section was 28¾ inches tall with 24 inches of packing. The packing was made of 0.24" Pro-pak™ packing, supported by conical screens resting on rings welded to the internal diameter of the column. Distribution rings were also used at the top of each packed section to ensure even distribution of liquid from above, over the packing.

Still referring to FIG. 3, the feed point 80 was in the middle of the vertical height of solvent stripper column 3, between the first packed section 81 and the section packed section 82. A feed, depicted as stream 17 in FIG. 1, was added to the solvent stripper column 3 at the feed point 80. The solvent stripper column 3 was operated at 4 to 5 psig. The steam flow to the reboiler 83 at the base of the tower was controlled to hold the weight percentage of PO in the bottoms at 0.5 to 1.5 wt %. Vapor was removed from the top of the column, and fed to a total condenser. The condensed liquid was split into two parts. One part was fed back to the top of the solvent stripper column 3 as reflux. The rest of the liquid distillate was taken as PO product shown as stream 34 on FIG. 1.

EXAMPLES

The following examples were carried out in a continuous pilot plant. The overview of the pilot unit is shown in FIG. 1. Additional details of a solvent lights tower 1, used in the examples are shown in FIG. 2. Additional details of solvent stripper column 3 are shown in FIG. 3. The solvent lights tower 1 employed in the examples had a 2" inside diameter and contained a bed of Pro-pak™ stainless steel protruded packing that was 11 feet deep. The Pro-pak™ stainless steel protruded packing was 0.24" size. The solvent stripper 3 in FIG. 1 is also shown in more detail on FIG. 3. The solvent stripper was 3" inside diameter and contained a bed of Pro-pak™ stainless steel protruded packing, 0.24" size, which was 4 feet deep.

Example 1

Example 1 describes the test period when the pilot unit solvent lights tower 1 as shown in FIGS. 1 and 2 was operated first at 25 psig. The feed stream 10 comprising crude propylene oxide (an intermediate stream from a PO/TBA process) was fed to a point on the solvent lights tower 1 at the middle of the column. Table 5 shows the concentrations of key impurities in the feed stream, each expressed as a weight percentage of the total composition.

TABLE 5

| Component | Average weight percent |
|---|---|
| MeF | 0.06 |
| Methanol | 0.1172 |
| Acetaldehyde | 0.03 |
| Water | 0.16 |
| Formaldehyde | 0.005 |

A plurality of temperature probes, TE2112, TE2111, TE2110, TE2108, TE2107, TE2105, TE2113, TE2109, and TE2138 were employed and were positioned as shown in FIG. 2.

The temperature of the feed stream 10 was 27 degrees Celsius and the flow rate was 3.0 kg/hr. Entering at the top of the tower was stream 32, comprising a lean solvent, pumped from the bottom of the solvent stripper 3, shown in FIG. 1. The solvent stripper 3 is also shown in greater detail in FIG. 3. The flow rate of lean solvent in stream 32 was 21.5 kg/hr. The distillate, stream 11, from the solvent lights tower 1 was pumped back into the tower as reflux, stream 14, at a rate of 1.5 kg/hr.

The rest of the distillate, stream 13, was pumped into the water wash apparatus 2 at a rate of 185 gm/hr. Two other streams were fed to the water wash apparatus 2: deionized water at a rate of 100 gm/hr and lean solvent from the bottom of the solvent stripper at a rate of 2.4 kg/hr. The water wash apparatus 2 consisted of three parts: a mixer, a coalescer and a decanter. The mixer was a 4-inch section of ¹⁄₁₆" OD tubing having an inside diameter of 0.030". Downstream of the mixer was a coalescer (not illustrated) which was a 1-foot long bed of glass wool in a ⅜" OD tube. Downstream of the coalescer was a decanter (not illustrated) where the organic and aqueous phases were separated. The decanter was a vertical glass pipe, 2.0" ID by 12" tall. The washed organic phase overflowed from the top of the decanter and was sent to the top of the solvent lights tower 1. The aqueous bottom layer from the decanter, rich in methanol, methyl formate, acetaldehyde, and formaldehyde, was sampled and collected. The organic and aqueous products from the decanter were used to calculate partition coefficients for the key impurities, as shown in Table 6. Partition Coefficient for each component (i) was calculated based on the following definition:

TABLE 6

| Partition Coefficient = $\dfrac{\text{Weight fraction in Aqueous phase}}{\text{Weight fraction in Organic phase}}$ | |
|---|---|
| Component | Average Partition Coefficient |
| Methyl Formate | 1.6 |
| Methanol | 57 |
| Acetaldehyde | 6.6 |
| PO | 0.8 |
| Formaldehyde | 190 |

Table 6 shows that methanol, acetaldehyde and formaldehyde are easily extracted by the water wash block, since the partition coefficients are high.

Table 7 provides exemplary temperature, pressure and flow rate data for the pilot unit operation.

TABLE 7

| Stream | Temperature | Pressure | Flow Rate |
|---|---|---|---|
| 10 | 69-84° C. | 25-30 psig | 2.7-3.3 kg/hr |
| 11 | 77-84° C. | 25-30 psig | 1.65-1.72 kg/hr |
| 12 | 63-72° C. | 25-30 psig | 2-13 gm/hr |
| 13 | 50-68° C. | 25-30 psig | 160-200 gm/hr |
| 14 | 50-68° C. | 25-30 psig | 1.49-1.5 kg/hr |
| 15 | 106-119° C. | 25-30 psig | 24-28 kg/hr |
| 16 | 106-119° C. | 25-30 psig | |
| 17 | 16-20° C. | 25-30 psig | 24-28 kg/hr |
| 20 | 20-26° C. | 25-30 psig | 100-101 gm/hr |
| 21 | 43-46° C. | 25-30 psig | 2.3-2.8 kg/hr |
| 22 | 43-46° C. | 25-30 psig | 102-118 gm/hr |
| 31 | 20-26° C. | 25-30 psig | 22.2-25.6 kg/hr |
| 32 | 20-26° C. | 25-30 psig | 20-23 kg/hr |
| 33 | 20-26° C. | 25-30 psig | 2.2-2.6 kg/hr |
| 34 | 69-84° C. | 3-4 psig | 2.7-3.3 kg/hr |

The vapors from the solvent lights tower 1, which did not condense in cooler 61 shown in FIG. 2 were collected and analyzed. The bottoms 17 from the solvent lights tower 1 were sent to the middle of the solvent stripper tower 3, as shown FIG. 1. The solvent stripper tower 3 was operated at 4 psig. The purpose of the solvent stripper tower 3 was to recover the propylene oxide product as a distillate (overhead) stream 34 and the lean solvent as the bottoms stream 31. The feed rate to the solvent stripper tower 3 was 26.9 kg/hr. The reflux rate to the solvent stripper tower 3 was 8.0 kg/hr. As mentioned earlier, the bottoms product 31 from the solvent stripper tower 3 was split into two streams (stream 32 and stream 33), one feeding the top of the solvent lights tower and the other feeding the wash block mixer, shown as unit 2 on FIG. 1.

As the pressure of the solvent lights tower 1 was increased from 25 psig to 30 psig, the operating temperatures at the solvent-light column 1 also increased by about 5 degrees Celsius. At higher column temperature, a large amount of hemiacetals and/or acetals are converted to the form of aldehyde plus alcohol. Aldehyde and alcohol are then distilled overhead in the solvent lights tower and removed by both water wash and vapor purge.

Formaldehyde is primarily removed into aqueous purge. Acetaldehyde is removed into both purges. As shown in Table 6 water wash operation, formaldehyde is favorably partitioning into the aqueous phase.

As shown in Table 8, with higher temperatures at the Solvent Lights Column 1, formaldehyde in the final pilot plant product (Solvent Stripper Overhead 34) is reduced from 25.4 ppm to 7.8 ppm and acetaldehyde is reduced from 6.4 ppm to 4.8 ppm. This was an unexpected and extremely beneficial result.

Example 2

Unexpectedly beneficial results can also be obtained by reducing the amount of water, methanol, and/or glycol concentration in the solvent-light column 1 feed. Two methanol (MeOH) concentrations were tested using the same pilot unit as describe in Example 1. One test used a propylene oxide feed containing 0.1172 wt % MeOH, as shown in Table 5. The other, test used a feed having 0.0032 wt % of MeOH, as shown in Table 9. The feed stream comprising propylene oxide feed stream was a crude PO stream from a PO/TBA process. Both Table 5 and Table 9 show the concentrations of key impurities in the feed stream, each expressed as a weight percentage of the total composition of a crude PO stream from a PO/TBA process.

TABLE 9

| Component | Average weight percent |
|---|---|
| MeF | 0.06 |
| Methanol | 0.0032 |
| Acetaldehyde | 0.03 |
| Water | 0.16 |
| Formaldehyde | 0.005 |

With reduced MeOH in PO feed, both formaldehyde and acetaldehyde removal was unexpectedly improved, as indicated by the reduced aldehyde level in solvent stripper overhead 34. Without wishing to be bound by theory, it is possible that the improvement is due to both enhanced aldehyde-propylene oxide vapor liquid equilibrium (VLE) and less carryover of hemiacetals or acetals into the solvent stripper 3 from the solvent-light column 1. Table 10 summarizes the results obtained.

TABLE 10

Impact of Methanol Concentration on Aldehyde Removal

| Crude | Solvent Light Column Overhead 13 | | Solvent stripper Overhead 34 | |
|---|---|---|---|---|
| PO Feed 10 wt % MeOH | Average Formaldehyde (wt %) | Average Acetaldehyde (wt %) | Average Formaldehyde (ppm) | Average Acetaldehyde (ppm) |
| 0.1172 | 0.0683 | 1.266 | 7.8 | 4.8 |
| 0.0032 | 0.0736 | 1.275 | 3.6 | 3.5 |

Although the present invention has been described in considerable detail with reference to certain preferred versions thereof, other versions are possible. Therefore, the spirit and scope of the appended claims should not be limited to the description of the preferred versions contained herein.

TABLE 8

Impact of Higher Distillation Pressure and Temperature on Aldehyde Removal

| | Solvent-Light Column 1 | | Solvent Light Column 1 Overhead 13 | | Solvent Stripper Overhead 34 | |
|---|---|---|---|---|---|---|
| Pressure (psig) | Solvent-Light Overhead 11 Temp (° C.) | Solvent-light bottom product 15 Temp (° C.) | Avg. Formaldehyde, (wt. %) | Avg. Acetaldehyde, (wt. %) | Average Formaldehyde (ppm) | Average Acetaldehyde (ppm) |
| 25 | 77.1 | 78.5 | 0.0422 | 1.222 | 25.4 | 6.4 |
| 30 | 82.1 | 83.1 | 0.0683 | 1.266 | 7.8 | 4.8 |

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C §112, sixth paragraph. In particular, the use of "step of in the claims herein is not intended to invoke the provisions of 35 U.S.C §112, sixth paragraph.

What is claimed is:

1. A method comprising:
   (i) feeding a crude propylene oxide stream through an extractive distillation column,
      wherein the crude propylene oxide stream comprises propylene oxide, tert-butanol, and water,
      wherein the distillation column is operated at a pressure in a range of greater than 25 to 50 psig, and
      wherein the extractive distillation column overhead is fluidly coupled to a water wash apparatus;
   (ii) separating the crude propylene oxide stream into an overhead stream and a bottoms product stream, wherein a portion of the overhead stream is mixed with water and a paraffin solvent in a static mixer to form a mixture, and wherein the mixture is fed to the water wash apparatus, wherein the water wash apparatus allows droplets of the mixture to coalesce and to separate in a top organic phase and a bottom aqueous phase, wherein the top organic phase is fed to the extractive distillation column overhead as part of a reflux, and wherein the bottom aqueous phase is removed for further treatment.

2. The method of claim 1, wherein the extractive distillation column uses $C_8$-$C_{20}$ paraffin as extractive solvent.

3. The method of claim 1, wherein the extractive distillation column is operated at a pressure in a range from 25 to 35 psig.

4. The method of claim 1, wherein the extractive distillation column is operated at a pressure of about 30 psig.

5. The method of claim 1, wherein the crude propylene oxide stream comprises from 0.001 to 0.5 wt % methanol, based on the total composition of the crude propylene oxide stream.

6. The method of claim 1, wherein the crude propylene oxide stream comprises about 0.0032 wt % methanol, based on the total composition of the crude propylene oxide stream.

7. The method of claim 1, wherein the crude propylene oxide stream is an intermediate stream from a propylene oxide and tert-butanol process.

8. The method of claim 1, wherein the process produces a stream comprising less than 50 ppm formaldehyde.

9. The method of claim 1, wherein the process produces a stream comprising less than 30 ppm acetaldehyde.

10. The method of claim 1, wherein the process produces a stream comprising less than 5 ppm formaldehyde.

11. The method of claim 1, wherein the process produces a stream comprising less than 4.8 ppm acetaldehyde.

12. The method of claim 1, wherein the extractive distillation column is fluidly coupled to a reboiler, wherein the reboiler is operated at a temperature in a range of from 70 to 150 degrees Celsius.

13. A method comprising:
   (i) feeding a crude propylene oxide stream through an extractive distillation column,
      wherein the crude propylene oxide stream comprises propylene oxide, tert-butanol, and water,
      wherein the distillation column is operated at a temperature in a range of from 70 to 150 degrees Celsius, and
      wherein the extractive distillation column overhead is fluidly coupled to a water wash apparatus,
   (ii) separating the crude propylene oxide stream into an overhead stream and a bottoms product stream, wherein a portion of the overhead stream is mixed with water and a paraffin solvent in a static mixer to form a mixture, and wherein the mixture is fed to the water wash apparatus, wherein the water wash apparatus allows droplets of the mixture to coalesce and to separate in a top organic phase and a bottom aqueous phase, wherein the top organic phase is fed to the extractive distillation column overhead as part of a reflux, and wherein the bottom aqueous phase is removed for further treatment.

14. The method of claim 13, wherein the distillation column is operated at a temperature in a range of from 80 to 120 degrees Celsius.

15. The method of claim 13, wherein the distillation column is operated at a temperature of about 115 degrees Celsius.

16. The method of claim 13, wherein the crude propylene oxide stream comprises from 0.001 to 0.1 wt % methanol, based on the total composition of the crude propylene oxide stream.

17. The method of claim 13, wherein the crude propylene oxide stream is an effluent stream from a propylene oxide and tert-butanol process.

18. The method of claim 13, wherein the process produces a stream comprising less than 25.4 ppm formaldehyde.

19. The method of claim 13, wherein the process produces a stream comprising less than 6.4 ppm acetaldehyde.

20. The method of claim 13, wherein the process produces a stream comprising less than 7.8 ppm formaldehyde.

21. The method of claim 13, wherein the process produces a stream comprising less than 4.8 ppm acetaldehyde.

* * * * *